United States Patent
Little, III et al.

(10) Patent No.: US 9,703,005 B2
(45) Date of Patent: Jul. 11, 2017

(54) DOWNHOLE SENSING VIA SWEPT SOURCE LASERS

(71) Applicant: JP3 Measurement, LLC, Austin, TX (US)

(72) Inventors: Joseph Paul Little, III, Austin, TX (US); Jordan Dwelle, Austin, TX (US); William Howard, Austin, TX (US)

(73) Assignee: JP3 Measurement, LLC, Austin, TX (US)

( * ) Notice: Subject to any disclaimer, the term of this patent is extended or adjusted under 35 U.S.C. 154(b) by 0 days.

(21) Appl. No.: 15/360,075

(22) Filed: Nov. 23, 2016

(65) Prior Publication Data

US 2017/0153355 A1    Jun. 1, 2017

Related U.S. Application Data

(60) Provisional application No. 62/260,697, filed on Nov. 30, 2015.

(51) Int. Cl.

| | |
|---|---|
| *G01B 11/24* | (2006.01) |
| *G01V 8/16* | (2006.01) |
| *G01B 9/02* | (2006.01) |
| *G01N 15/02* | (2006.01) |
| *G01V 8/18* | (2006.01) |
| *E21B 47/00* | (2012.01) |

(52) U.S. Cl.
CPC ............ *G01V 8/16* (2013.01); *E21B 47/0002* (2013.01); *G01B 9/02004* (2013.01); *G01B 9/02091* (2013.01); *G01N 15/0227* (2013.01); *G01V 8/18* (2013.01)

(58) Field of Classification Search
CPC ........ G01V 8/16; G01V 8/18; G01B 9/02004; G01B 9/02091; G01N 15/0227; E21B 47/0002
USPC ......................................................... 356/601
See application file for complete search history.

(56) References Cited

U.S. PATENT DOCUMENTS

| | | | | |
|---|---|---|---|---|
| 5,179,541 | A | * | 1/1993 | Weido .................. B06B 1/0215 367/69 |
| 5,652,617 | A | * | 7/1997 | Barbour ............. E21B 47/0002 348/85 |

(Continued)

FOREIGN PATENT DOCUMENTS

| | | |
|---|---|---|
| WO | 2013019959 A2 | 2/2013 |
| WO | 2013050791 A1 | 4/2013 |

*Primary Examiner* — Sunghee Y Gray
(74) *Attorney, Agent, or Firm* — DuBois, Bryant & Campbell, LLP; William D. Wiese

(57) ABSTRACT

Systems and methods for performing downhole analysis within a well bore employ a swept source laser that can be sent downhole to generate high resolution images of the well bore. Various embodiments can also determine other physical properties of a below ground structure. The swept source lasers can create images using low-coherence interferometry or optical coherence tomography. Systems and methods may also be used to determine fluid flow rates towards the sensor at discrete points, such as individual perforations, by measuring the Doppler effect on the light back-scattered from the fluid. Fluid flow information could also be extracted by measuring the phase shift of the light between subsequent light scans if a phase sensitive detection scheme is utilized.

12 Claims, 2 Drawing Sheets

(56) References Cited

U.S. PATENT DOCUMENTS

| | | | |
|---|---|---|---|
| 2009/0177094 A1* | 7/2009 | Brown | A61B 5/0066 600/476 |
| 2009/0225333 A1* | 9/2009 | Bendall | G01N 21/954 356/626 |
| 2011/0138903 A1* | 6/2011 | Large | E21B 17/1021 73/152.17 |
| 2012/0169841 A1* | 7/2012 | Chemali | E21B 47/0002 348/36 |
| 2015/0167447 A1 | 6/2015 | Tjhang et al. | |

* cited by examiner

DOWNHOLE SENSING VIA SWEPT SOURCE LASERS

PRIORITY STATEMENT

Under 35 U.S.C. §119 & 37 C.F.R. §1.78

This non-provisional application claims priority based upon prior U.S. Provisional Patent Application Ser. No. 62/260,697 filed Nov. 30, 2015 in the names of Joseph Paul Little, Jordan Dwelle and William Howard, entitled "DOWNHOLE SENSING VIA SWEPT SOURCE LASERS," the disclosure of which is incorporated herein in its entirety by reference as if fully set forth herein.

BACKGROUND OF THE INVENTION

As drilling for oil and gas reserves has become more complicated and expensive, the need for high resolution images and diagnostic information about the well bore itself has greatly increased. Many downhole tools are currently used to classify properties of the rock, production characteristics of a well, and the completed infrastructure in place on a well bore, but the information is greatly susceptible to different interpretations. For example, different geologists can look at the same well log and derive three completely different interpretations of how the well should be produced and what the characteristics of that production will look like. Furthermore, downhole production measurements are only able to estimate what zones are the most productive and what their individual contributions are to the overall production of the well. The resolution of these production logs leaves a lot to be desired. Similarly, the instrumentation used to inspect the in-place production casing and tubing suffer from resolution issues and are unable to measure some of the more critical characteristics, such as coating thickness and joint integrity.

Horizontal drilling coupled with fracking has greatly expanded the potential production from rock formations. Each frack stage has multiple well bore perforations that allow the frack solution to enter into the formation and fracture, or crack open, the rock to release the hydrocarbons. However, it has been discovered that not all of the perforations become active upon initial injection. In fact, typically only a minority percentage of them actually become conduits for the frack solution to enter the formation and break open the rock, thus releasing the hydrocarbon content of only the active perforations. The result is a large amount of the overall well bore remains unused, but the ability to determine what specific perforations are not active is very difficult.

In addition to the production yield limitations associated with modern drilling, there is also significant need for high resolution imaging of the well bore to help troubleshoot issues with producing wells. These issues can include, but are not limited to, such things as scaling build up in the well, casing integrity, paraffin build up, water contamination, completion design, production tubing issues, leaks, and collapsed sections, just to name a few.

There is a need therefore for a method and system capable of generating a high resolution image of a well bore for inspecting and monitoring activity, including the amount and location of fracking and the degradation of the well bore.

SUMMARY OF THE INVENTION

The present invention relates to a device that can be sent downhole to generate high resolution images of a well bore, well casing, or other drilled structures below ground by utilizing swept source lasers. Various embodiments can also determine other physical properties of a below ground structure. The swept source lasers can create images using low-coherence interferometry ("LCI") or optical coherence tomography ("OCT"). These imaging techniques can be used to create a high resolution surface profile of the pipe showing, for example, the size of perforations, coating thickness, or pipe surface damage. The laser sweep range can vary from 20 nm to 300 nm depending on the resolution and should be centered on a region know not to be absorbed by the fluids in the well, such as water and hydrocarbon fluids. A good center range could start between 1500 nm to 1550 nm.

In various embodiments of the present invention, the swept source lasers may be used to determine fluid flow rates towards the sensor at discrete points, such as individual perforations, by measuring the Doppler effect on the light back-scattered from the fluid. Fluid flow information could also be extracted by measuring the phase shift of the light between subsequent light scans if a phase sensitive detection scheme is utilized. Suspended particulate size and distribution matrix information is also available.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

For a more complete understanding of the present invention, and the advantages thereof, reference is now made to the following descriptions taken in conjunction with the accompanying drawings, in which.

Figure 1:
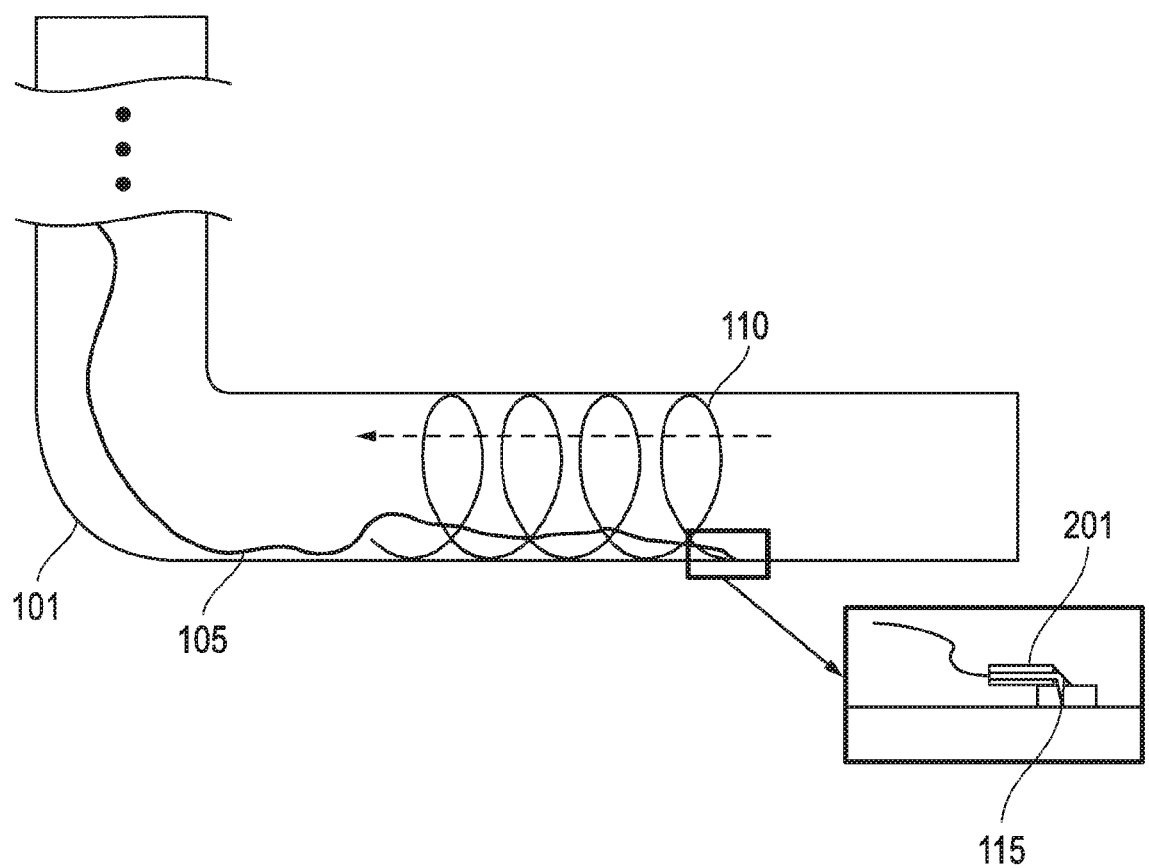
FIG. 1 depicts one embodiment of a swept source laser of the present invention in a well bore, including the rotating imaging head that is retracted during use resulting in a spiral path of the imaging head.

The figures are not necessarily to scale. The emphasis is, instead, placed upon illustrative principles. The figures are to be considered illustrative in all respects and are not intended to limit the invention, the scope of which is defined only by the claims.

DESCRIPTION OF THE PREFERRED EMBODIMENTS

The present invention is directed to improved methods and systems for, among other things, downhole sensing via swept source layers. "Swept source" refers to the type of laser incorporated into the device. A swept source laser sweeps across a narrow band of wavelengths as it cycles through its scanning range. The configuration and use of the presently preferred embodiments are discussed in detail below. It should be appreciated, however, that the present invention provides many applicable inventive concepts that can be embodied in a wide variety of contexts other than downhole sensing via swept source layers. Accordingly, the specific embodiments discussed are merely illustrative of specific ways to make and use the invention, and do not limit the scope of the invention.

Methods and systems described herein relate to a device that can be sent downhole to generate high resolution images of a well bore, well casing, or other drilled structures below ground, all of which are collectively referred to herein as a "well bore," by utilizing swept source lasers. Various embodiments can also determine other physical properties of a below ground structure.

The swept source lasers can create images using low-coherence interferometry ("LCI") or optical coherence tomography ("OCT"). LCI is a non-contact optical sensing technology in which an optical probe directs a low-coherence light beam at a sample surface and sends reflected light signals back to the interferometer. When the sample surface has varying depths, light is simultaneously reflected back from the top and bottom of each depth. The reflected optical data from each single scan point is interpreted by the interferometer as an interference pattern and recorded as a depth profile. By scanning the probe in a linear fashion across the sample surface, a cross-section is obtained. 3D volumetric images can be generated by combining multiple cross-sections.

OCT is also a non-contact optical sensing technology that synthesizes cross-sectional images from a series of laterally adjacent depth-scans. At present OCT is used in three different fields of optical imaging, in macroscopic imaging of structures which can be seen by the naked eye or using weak magnifications, in microscopic imaging using magnifications up to the classical limit of microscopic resolution and in endoscopic imaging, using low and medium magnification. First, OCT techniques, like the reflectometry technique and the dual beam technique were based on time-domain low coherence interferometry depth-scans. Later, Fourier-domain techniques have been developed and led to new imaging schemes. Recently developed parallel OCT schemes eliminate the need for lateral scanning and, therefore, dramatically increase the imaging rate. These schemes use CCD cameras and CMOS detector arrays as photodetectors. Video-grade three-dimensional OCT pictures have been obtained. Modifying interference microscopy techniques has led to high-resolution optical coherence microscopy that achieved sub-microscopic resolution.

OCT can be used to create a high resolution surface profile of the pipe showing the size of perforations, coating thickness, or pipe surface damage. The OCT signal can also be used to determine fluid flow rates towards the sensor at discrete points, such as individual perforations, by measuring the Doppler effect on the light back-scattered from the fluid. Fluid flow information could also be extracted by measuring the phase shift of the light between subsequent light scans if a phase sensitive detection scheme is utilized. Suspended particulate size and distribution matrix information is also available.

As previously mentioned, embodiments of the device of the present invention can be sent downhole to generate high resolution images of a well bore. Various embodiments of the device include a laser imaging head that is fiber optically coupled to the laser source or laser sources and taken down the well bore via coil tubing, downhole tractor, or other methods known in the art that are capable of entering in the well bore and navigating the entire length thereof. In some embodiments, the optical head rotates inside the well bore in order to generate the high resolution images. The head is inserted in the well bore and then extracted therefrom while the swept source laser is gathering data.

In some embodiments, the device includes a fluid-emitting nozzle or other spray device in front of the optical head to inject a fluid to dilute or displace the existing contents of the well bore in order to provide the most high resolution image possible. Referring now to FIG. 1 in which a fiber optic cable 105 is inserted into a well bore 101. An imaging head 115 is attached to the fiber optic cable 105. The imaging head 115 is inserted in the well bore 101 and then, as it is removed, the swept source lasers are taking readings.

Figure 2:
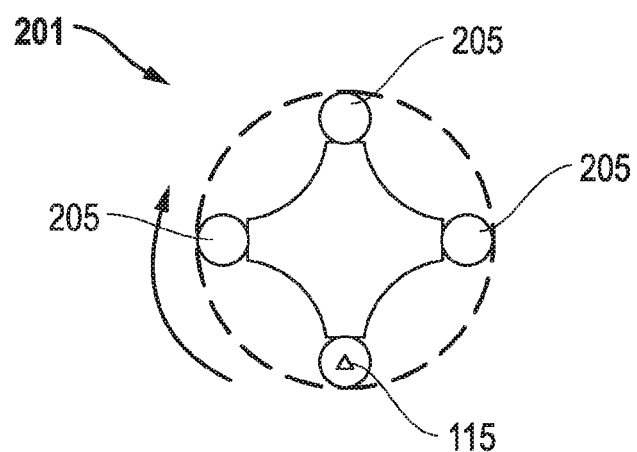
FIG. 2 depicts one embodiment of the imaging head of the present invention.
Figure 3:
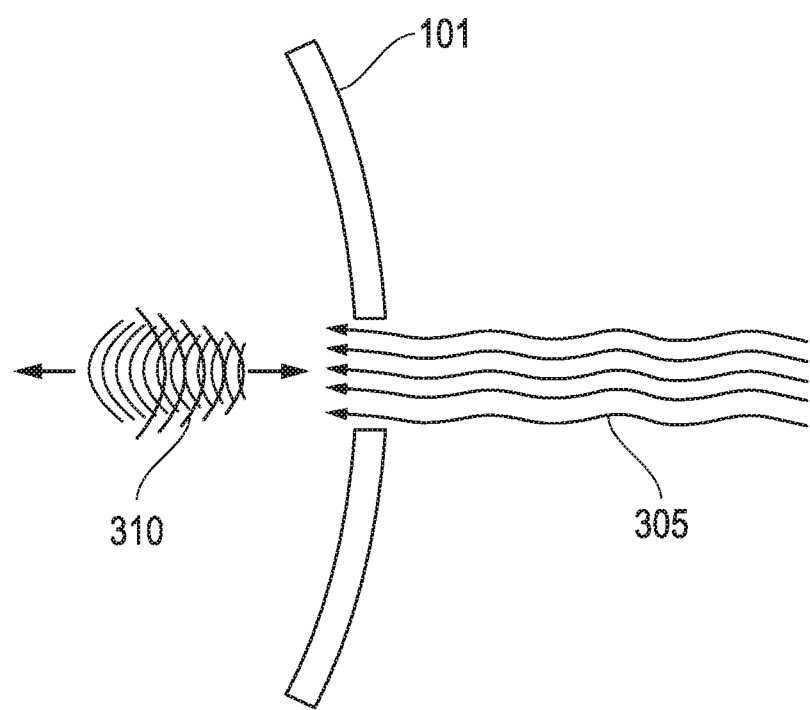
FIG. 3 depicts the manner in which an imaging head detects properties of a flowing material using a Doppler shifted reflection.

As shown in FIG. 2, a head assembly 201 may be positioned on the end of the fiber optic cable 105, and the head assembly 201 may have multiple nozzles. In the illustrated example, the head assembly 201 has both nozzles and an imaging head. The imaging head 115 depicted in FIG. 3 is configured with three fluid injection nozzles 205 and an imaging head 115, although imaging heads used in connection with the present invention may have more or fewer nozzles. As previously mentioned, the imaging head 115 rotates as it is removed from the well bore and, in the configuration show in FIG. 2, the head is rotating in the clockwise direction, however, rotation may also be in the counterclockwise direction without altering the efficacy of the present invention.

In various embodiments, it may be desirable for lasers to have an optical frequency bandwidth capable of generating an interference pattern that may be translated into a high resolution image. To operate properly in most downhole applications, the imaging head must be designed to withstand the high temperatures and pressures present in a well bore.

In operation, the light reflected from the well bore surface will interfere with light from a known reference path in an interferometer, such as the previously described interferometers used with LCI or OCT. The path length delay between these two paths will create an interference pattern which can be interpreted to extract information about the distance and speed of the light scattering surface. In some embodiments, this interferometer may be sent down the well bore. In other embodiments, the interferometer may be outside the well bore at the well surface, with only the sample light being sent down the well bore through the fiber optic cable to the imaging site.

While embodiments of the present invention may be used or useful in obtaining information about the well bore's surface, in other embodiments the imaging head 115 may be temporarily stopped as it is being withdrawn from the well bore in order to determine fluid flow rates and particle size distribution in the produced fluid at specific points. It may also be stopped to focus in on a specific joint, coupling, or identified anomaly in the production infrastructure of the well bore. Referring now to FIG. 3 which depicts the Doppler-shifted reflection 310 of a light emitted from an imaging head (not shown) towards an approaching fluid 305. The reflection 310 can be utilized to extract valuable information about the fluid 310, such as, for example, the amount of suspended solids, including sand and other proppant materials introduced in the fracking process. Particle size and the relative distribution of these solids may also be determined and presented as a function of the whole fluid composition.

Using the methods and systems of the present invention, images and other diagnostic information may be used to create a very accurate profile of an existing well bore. For example, the information from the device can be used to determine which well bore perforations are active and how much fluid is being contributed by an individual perforation. All of this information can be used to design a secondary (or many subsequent) fracking operations that isolate depleted zones and activate new zones on existing wells. The aggregated information can also be used to formulate an entirely new fracking solution for future wells.

The information can also be used to identify issues within the well bore that would otherwise be very difficult to determine and isolate. For example, if a well is exhibiting scaling problems or paraffin build up, images can be taken before and after treatment methodologies have been implored to determine their efficacy. Coatings can be examined to ensure safe operating conditions and problems with the casing or production tubing can be specifically identified and therefore repaired much more efficiently than a total rework of the completion equipment that is currently required.

Because the majority of the expense of bringing a well on-line includes the land acquisition cost, mineral lease expense, drilling the vertical section of the well, and surface production equipment; any ability to increase the overall production of a single well bore is highly desirable. The ability to accurately ensure that a majority of the productive section of a well is utilized can dramatically affect the value proposition of a project.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for downhole sensors known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

We claim:

1. A method for creating a high resolution image by low coherence interferometry of the surface of a well bore, comprising:
   placing the distal end of a fiber optic cable into a well bore while the proximal end of the fiber optic cable remains out of the well bore, wherein the fiber optic cable is configured with a head assembly affixed to the distal end thereof, the head assembly including at least a swept source laser scanner;
   removing the fiber optic cable from the well bore while the head assembly rotates in a circular direction;
   scanning the surface of the well bore with the swept source laser scanner;
   using the information received from the swept source laser scanner to create a high resolution image of the surface of the well bore using low coherence interferometry.

2. The method of claim 1, wherein the low coherence tomography is optical coherence tomography.

3. The method of claim 1, wherein the interferometer is located in the head assembly with the swept source laser scanner.

4. The method of claim 1, wherein the interferometer is located at the proximal end of the fiber optic cable and is communicatively coupled to the swept source laser scanner through the fiber optic cable.

5. The method of claim 1, wherein the head assembly includes one or more fluid-emitting nozzles that dilute or displace the existing contents of the well bore in order to improve the efficacy of the swept source laser scanner.

6. The method of claim 1, wherein the circular motion of the head assembly is clockwise.

7. A system for creating a high resolution image by low coherence interferometry of the surface of a well bore, comprising:
   a fiber optic cable having a proximal end and a distal end;
   a head assembly affixed to the distal end of the fiber optic cable;
   at least one swept source laser scanner included within the head assembly;
   wherein, the head assembly is placed into a well bore while the proximal end of the fiber optic cable remains out of the well bore and, as the fiber optic cable is removed from the well bore, the head assembly rotates in a circular direction while scanning the surface of the well bore with the swept source laser scanner, and information from the swept source laser scanner is used to create a high resolution image of the surface of the well bore using low coherence interferometry.

8. The system of claim 7, wherein the low coherence interferometry is optical coherence tomography.

9. The system of claim 7, wherein the interferometer is located in the head assembly with the swept source laser scanner.

10. The system of claim 7, wherein the interferometer is located at the proximal end of the fiber optic cable and is communicatively coupled to the swept source laser scanner through the fiber optic cable.

11. The system of claim 7, wherein the head assembly includes one or more fluid-emitting nozzles that dilute or displace the existing contents of the well bore in order to improve the efficacy of the swept source laser scanner.

12. The system of claim 7, wherein the circular motion of the head assembly is clockwise.

* * * * *